United States Patent
Heukensfeldt Jansen et al.

(10) Patent No.: US 8,487,265 B2
(45) Date of Patent: Jul. 16, 2013

(54) IMAGING DETECTOR AND METHOD OF MANUFACTURING

(75) Inventors: Floribertus P. M. Heukensfeldt Jansen, Ballston Lake, NY (US); Yaron Hefetz, Kibbutz alonim (IL)

(73) Assignee: General Electric Company, Niskayuna, NY (US)

( * ) Notice: Subject to any disclaimer, the term of this patent is extended or adjusted under 35 U.S.C. 154(b) by 49 days.

(21) Appl. No.: 13/304,248

(22) Filed: Nov. 23, 2011

(65) Prior Publication Data

US 2013/0126744 A1    May 23, 2013

(51) Int. Cl.
*H01L 27/146* (2006.01)
(52) U.S. Cl.
USPC .................................................. 250/370.08
(58) Field of Classification Search
USPC ....... 250/370.01–370.15, 362, 363.01–363.1, 250/394; 378/98.8
See application file for complete search history.

(56) References Cited

U.S. PATENT DOCUMENTS

| | | | |
|---|---|---|---|
| 6,838,672 B2 | 1/2005 | Wagenaar et al. | |
| 7,166,846 B2 | 1/2007 | Engdahl et al. | |
| 7,291,841 B2 | 11/2007 | Nelson et al. | |
| 7,569,826 B2 | 8/2009 | Uribe et al. | |
| 7,671,340 B2 | 3/2010 | Uribe et al. | |
| 8,143,585 B2 * | 3/2012 | Guerin et al. | 250/370.09 |
| 2007/0228282 A1 | 10/2007 | Habteet et al. | |
| 2010/0282977 A1 | 11/2010 | Dey et al. | |
| 2010/0308226 A1 | 12/2010 | Zeng | |

OTHER PUBLICATIONS

Qian et al., "A Small-Animal Imaging System Capable of Multi-pinhole Circular/Helical SPECT and Parallel-Hole SPECT", Nuclear Instruments and Methods in Physics Research Section A: Accelerators, Spectrometers, Detectors and Associated Equipment, vol. 594, Issue 1, pp. 102-110, Aug. 21, 2008.
Goorden et al., "High-Resolution Tomography of Positron Emitters with Clustered Pinhole SPECT", Physics in Medicine and Biology, vol. 55, pp. 1265-1277, 2010.

* cited by examiner

*Primary Examiner* — Kiho Kim
(74) *Attorney, Agent, or Firm* — Marie-Claire B. Maple

(57) ABSTRACT

Imaging detectors and methods of manufacturing are provided. One imaging detector includes a first detector layer within a detector module and a second detector layer within the detector module and spaced apart from the first detector layer, wherein the second detector layer has an opening therethrough. The imaging detector also includes a collimator mounted to the detector module, wherein the collimator is one of a single pinhole collimator or a multi-pinhole collimator. Additionally, the second detector layer is mounted within the detector module closer to an opening of the collimator than the first detector layer.

23 Claims, 18 Drawing Sheets

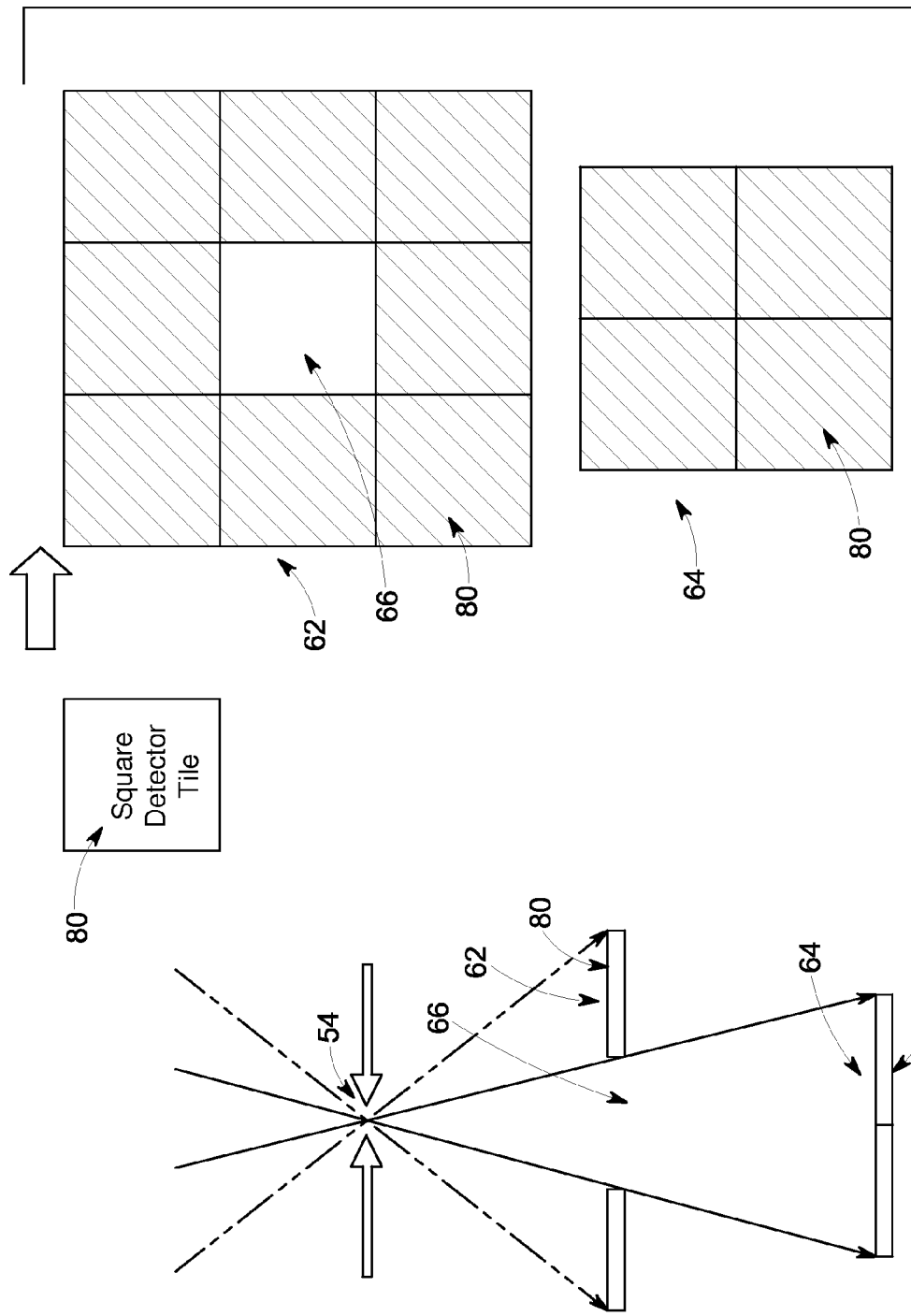

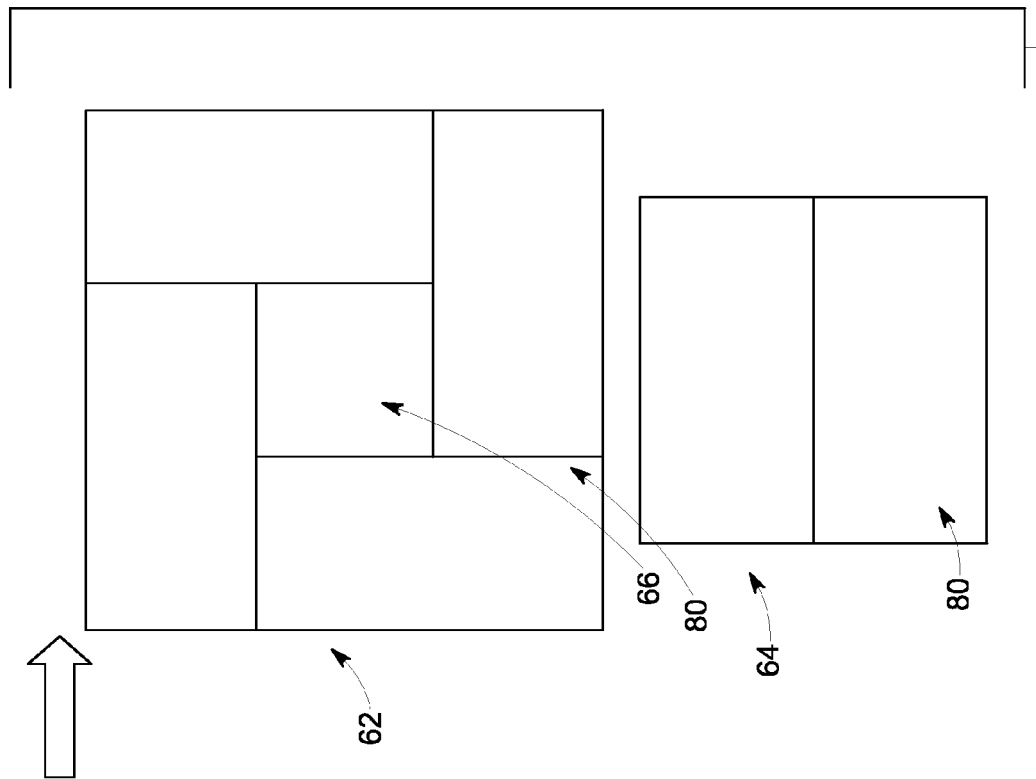
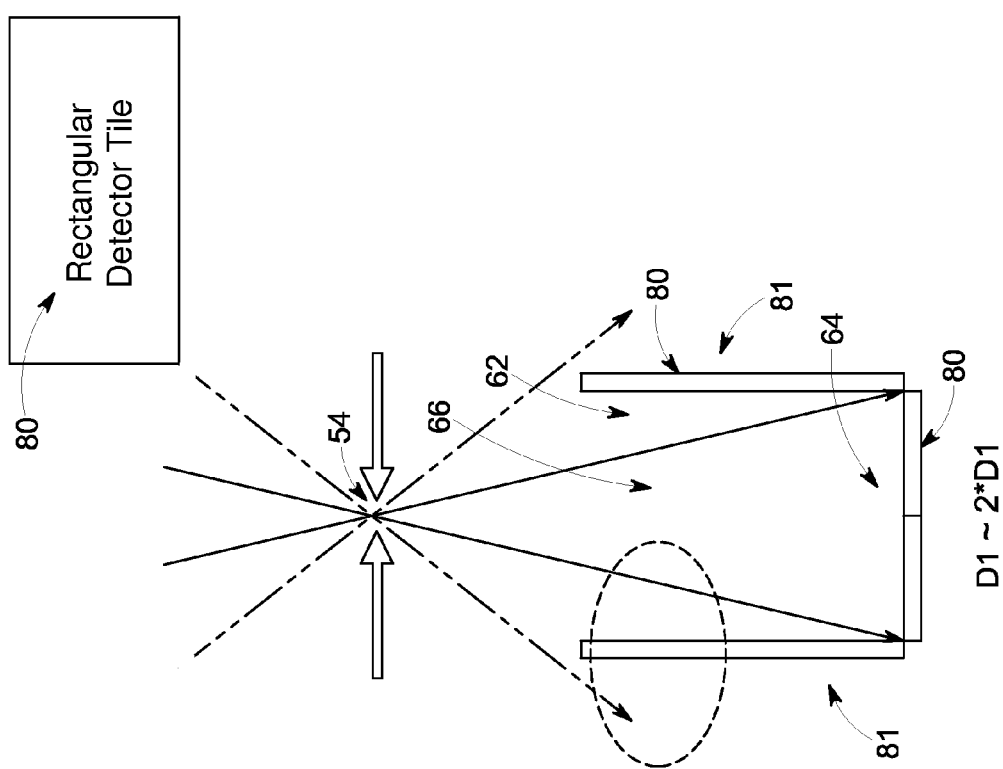

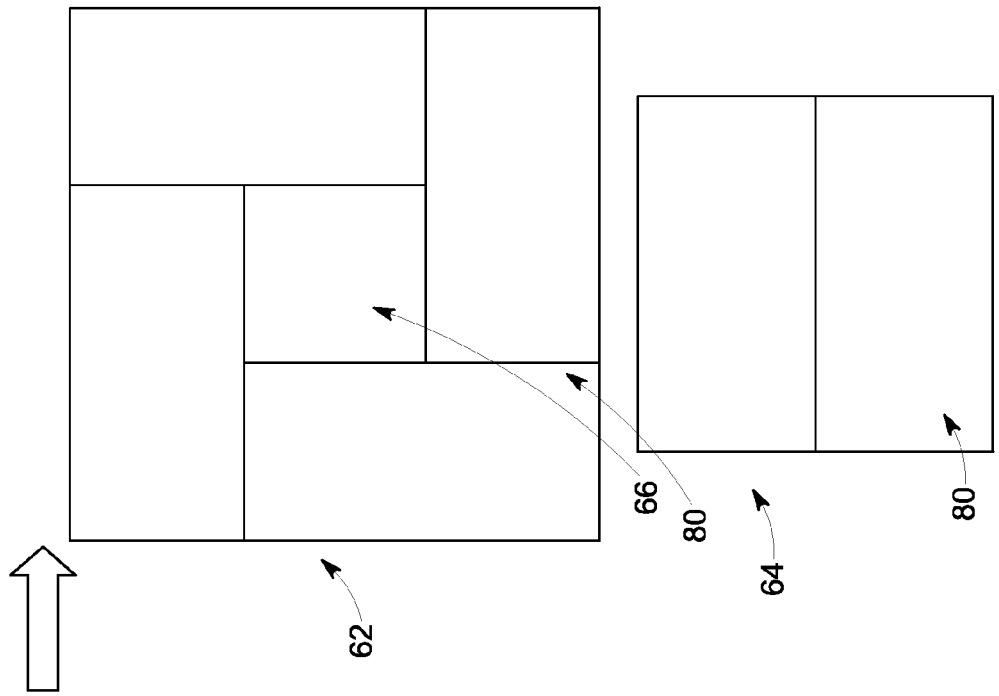
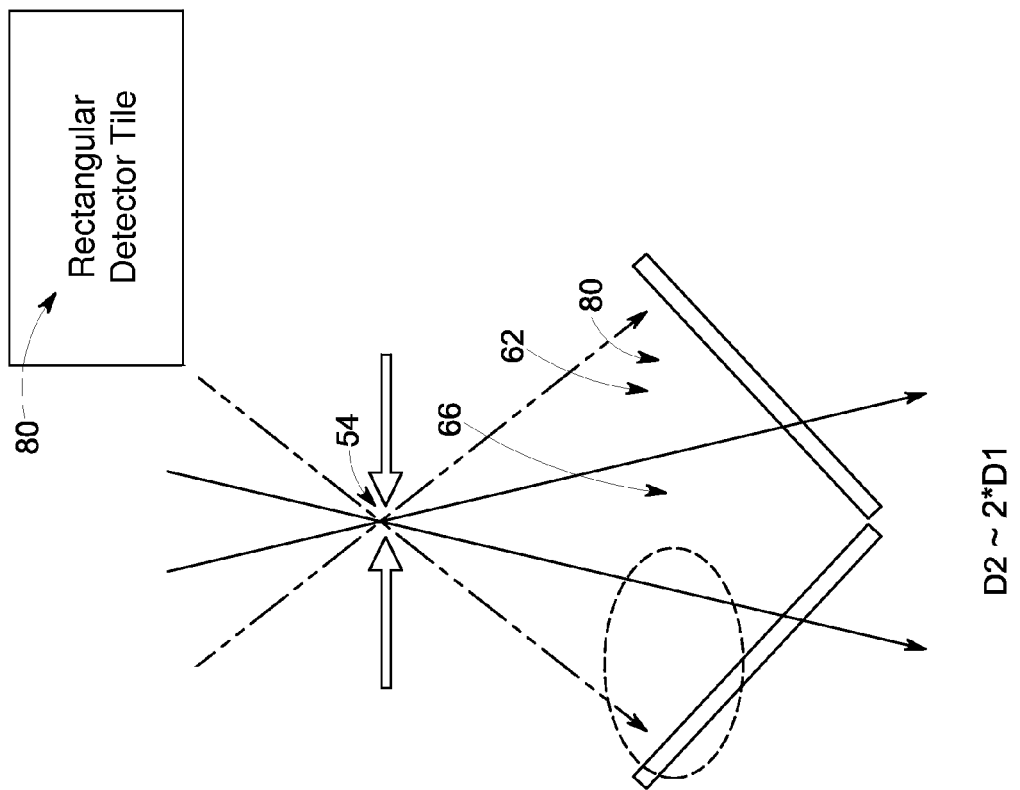

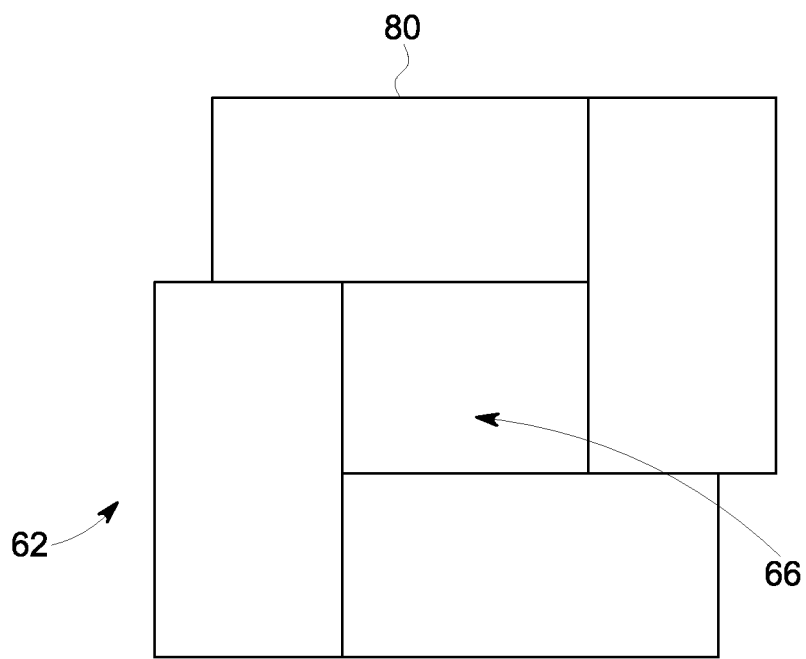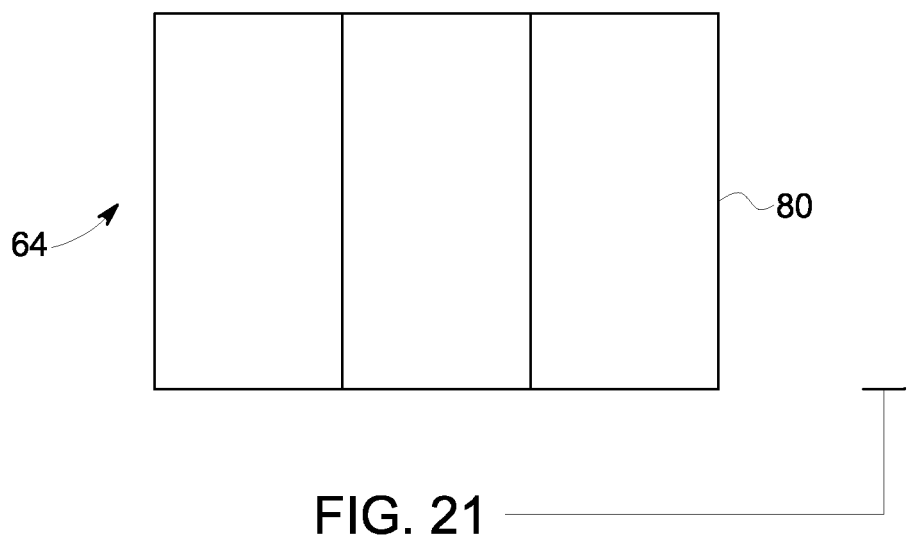
FIG. 21

IMAGING DETECTOR AND METHOD OF MANUFACTURING

BACKGROUND

In NM imaging, radiopharmaceuticals are injected into a person and then detectors (e.g., gamma cameras), typically mounted on a gantry, capture and form images from the radiation emitted by the radiopharmaceuticals. The NM images primarily show physiological function of, for example, a patient or a portion of a patient being imaged.

Collimation may be used to create an image of radiation-emitting objects in the field of view of the detectors. Different types of collimation are known, for example, different shapes and configurations of collimators are known for use in different types of applications. However, when designing collimators a tradeoff exists between resolution and sensitivity. For example, a high-resolution collimator views a very narrow column of activity from the patient, and therefore provides high spatial resolution, but at a reduced sensitivity. In contrast, a high sensitivity collimator accepts radiation from a wider range of angles, which increases the sensitivity, but reduces resolution. Thus, depending on desired or required imaging characteristics or properties, collimators are designed to provide resolution and sensitivity levels to maximize or optimize imaging based on the desired or required characteristics or properties. However, such designs may perform unsatisfactorily in different applications.

As one example, in pinhole collimators, such as for Single Photon Emission Computed Tomography (SPECT) imaging detectors, the field of view of the detector depends on the size of the detector and the focal length of the collimator. Thus, there is a tradeoff between field of view, resolution, sensitivity, and detector area.

Accordingly, known collimator designs often require one or more compromises. Thus, these designs may result in detectors that have less than optimal imaging for a particular application.

BRIEF DESCRIPTION

In accordance with an embodiment, a nuclear medicine (NM) imaging detector is provided that includes a first detector layer within a detector module and a second detector layer within the detector module and spaced apart from the first detector layer, wherein the second detector layer has an opening therethrough. The NM imaging detector also includes a collimator mounted to the detector module, wherein the collimator is one of a single pinhole collimator or a multi-pinhole collimator. Additionally, the second detector layer is mounted within the detector module closer to an opening of the collimator than the first detector layer.

In accordance with another embodiment, a nuclear medicine (NM) imaging system is provided that includes a gantry, at least one imaging detector supported on the gantry and configured to rotate about the gantry defining an axis of rotation, and at least one detector module forming the imaging detector. The detector module includes a first detector layer and a second detector layer spaced apart from the first detector layer, wherein the second detector layer has an opening therethrough. The detector module also includes a pinhole collimator mounted thereto, wherein the second detector layer is mounted within the detector module closer to the pinhole collimator than the first detector layer.

In accordance with yet another embodiment, a nuclear medicine (NM) imaging system is provided that includes a plurality of imaging detectors. The detector modules include a first detector layer and a second detector layer spaced apart from the first detector layer, wherein the second detector layer has an opening therethrough. The detector modules also include a pinhole collimator mounted thereto, wherein the second detector layer is mounted within the detector module closer to the collimator than the first detector layer.

In accordance with still another embodiment, a method of manufacturing a detector is provided. The method includes forming multiple detector layers with at least one layer having an opening therethrough and aligning the multiple detector layers spaced apart within a detector module. The method also includes mounting the detector layers within the detector module with a pinhole collimator mounted thereto, with the detector layer with the opening mounted closer to an opening of the pinhole collimator.

BRIEF DESCRIPTION OF THE DRAWINGS

FIGS. 7 and 8 are diagrams illustrating detector tiles forming detector layers in accordance with other various embodiments.

FIGS. 14 and 15 are diagrams illustrating detector tiles forming detector layers in accordance with other various embodiments.

FIGS. 16 and 17 are diagrams illustrating detector tiles forming detector layers in accordance with other various embodiments.

FIG. 21 is a diagram illustrating detector tiles forming detector layers in accordance with other various embodiments.

DETAILED DESCRIPTION

Figure 1:
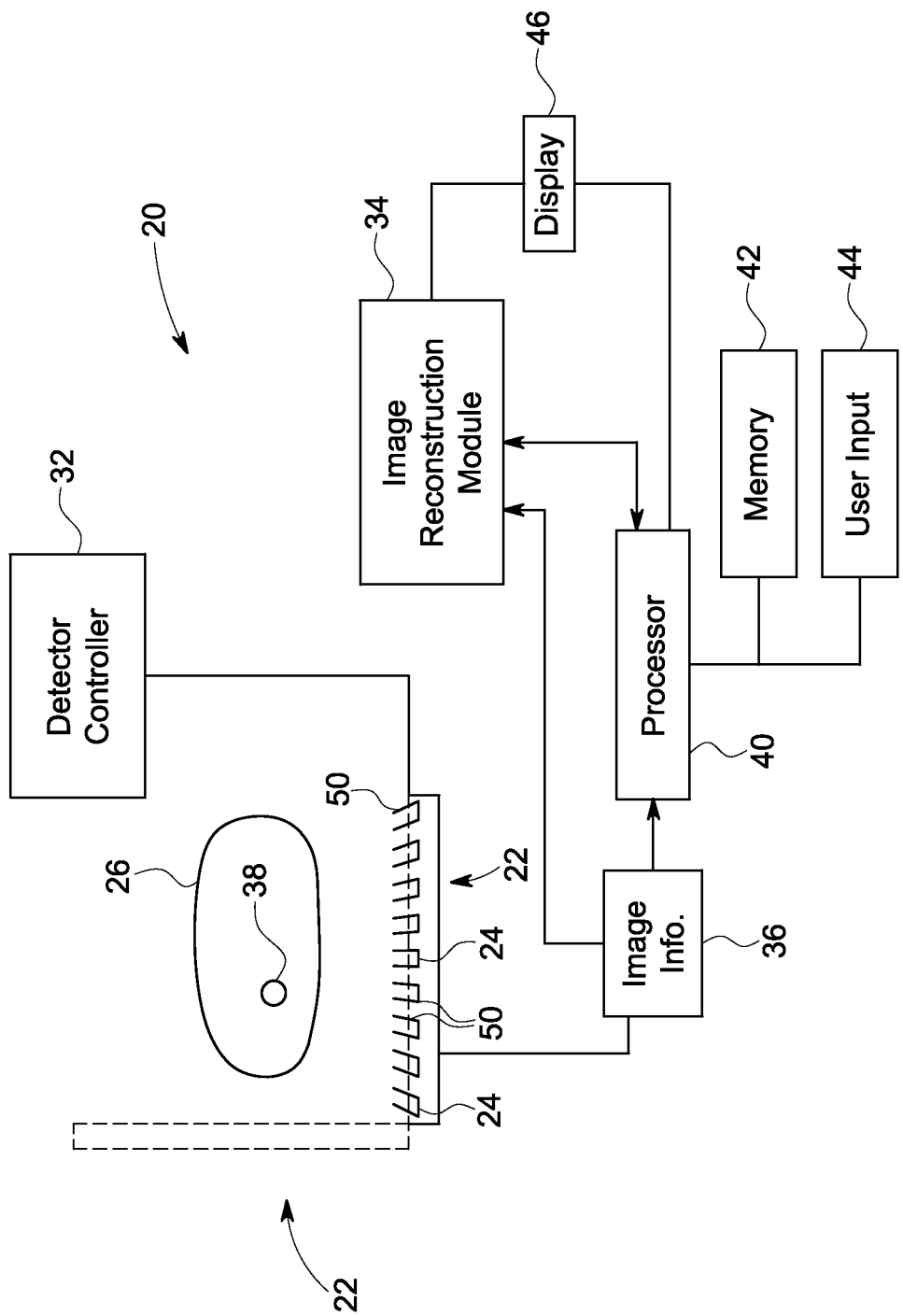
FIG. 1 is a simplified block schematic diagram of an imaging system in accordance with an embodiment.

The following detailed description of certain embodiments, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Also as used herein, the phrase "reconstructing an image" is not intended to exclude embodiments in which data representing an image is generated, but a viewable image is not. Therefore, as used herein the term "image" broadly refers to both viewable images and data representing a viewable image. However, many embodiments generate, or are configured to generate, at least one viewable image.

Various embodiments provide detectors for imaging systems, such as diagnostic imaging systems (e.g., Nuclear Medicine (NM) imaging systems). For example, a multi-layer detector arrangement may be provided for use in a Single Photon Emission Computed Tomography (SPECT) imaging system. In some embodiments, detector arrangements provide a multi-layer (e.g., dual layer) configuration that may form part of a pinhole detector module. By practicing at least one embodiment, increased high frequency sampling of the image space may be provided. At least one technical effect of at least one embodiment is an improved tradeoff between field of view, resolution, sensitivity, and detector area for imaging detectors.

Various embodiments may be implemented in different types of imaging systems, such as NM imaging systems having different arrangements and configurations of gamma cameras, for example, different types of SPECT systems. For example, various embodiments provide Cadmium Zinc Telluride (CdZnTe or CZT) SPECT cameras that provide increased resolution sampling of a central field of view (FOV) while providing a larger FOV with limited or reduced resolution sampling using a smaller amount of detector material. It should be noted that the various embodiments are not limited to CZT SPECT cameras and other imaging detectors, for example, other gamma cameras may embody the various embodiments, including detectors formed from different materials, such as Sodium Iodide (NaI), among others. Additionally, the various embodiments may be implemented in connection with other types of NM imaging systems, such as Positron Emission Tomography (PET) systems, as well as with dual-modality imaging systems.

Figure 2:
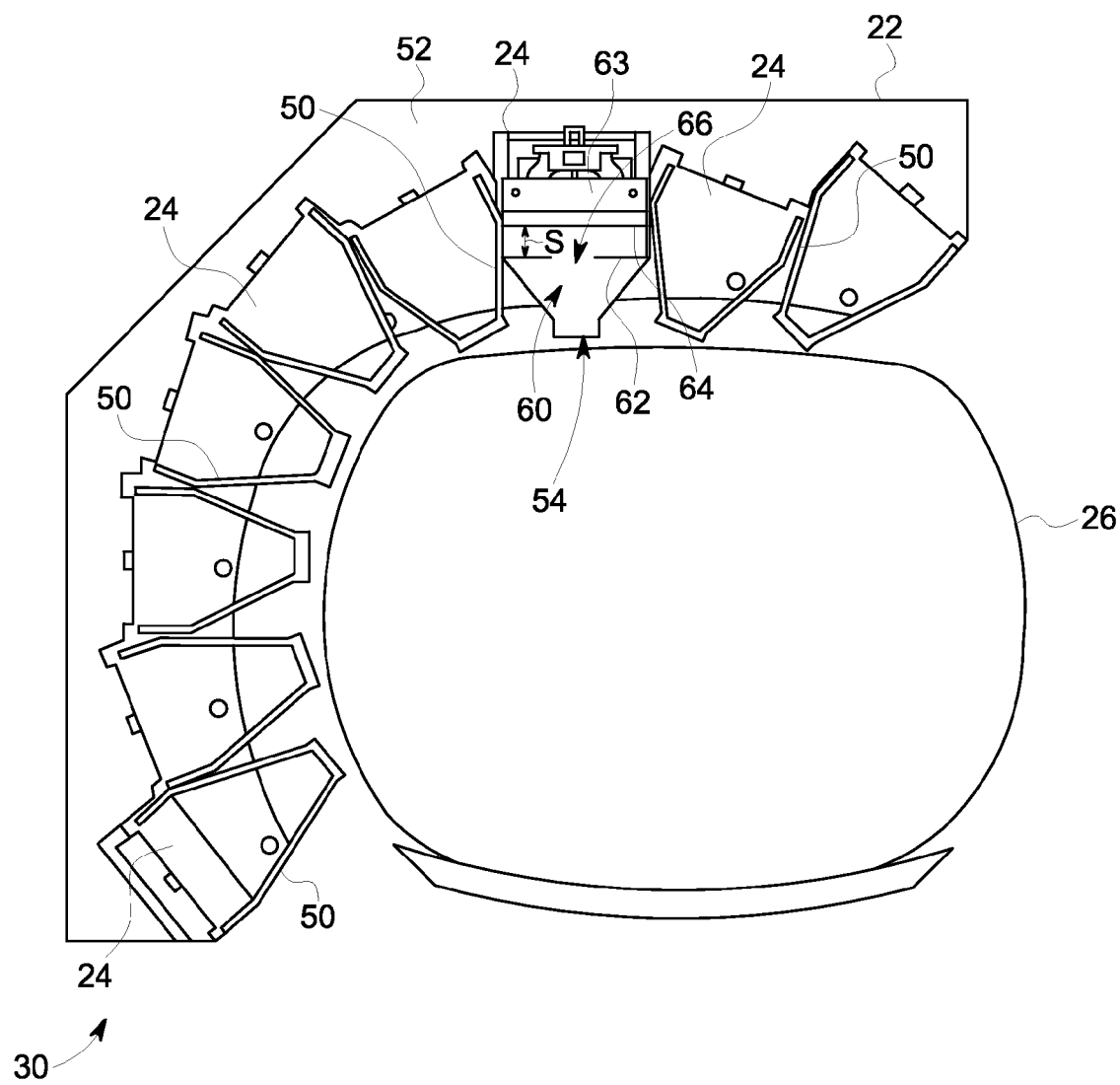
FIG. 2 is a diagram illustrating detector modules fowled in accordance with various embodiments.

An NM imaging system 20 may be provided as illustrated in FIG. 1 having an NM camera configured as a SPECT detector housing 22, which in this embodiment includes a plurality of detector modules 24 having a multi-layer configuration as described in more detail herein. It should be noted that the various embodiments are not limited to the NM imaging system 20 having a single camera or detector housing 22 operable to perform SPECT imaging. For example, the NM imaging system 20 may include one or more additional cameras of detector housings 22 (one additional detector housing 22 is shown in dashed lines). An object, such as a patient 26, is positioned in proximity to the one or more detector housings 22 for imaging. It should be noted that the detector modules 24 in various embodiments, for example as shown in FIG. 2, may be aimed such that the detector modules 24 share a FOV. It also should be noted that the detector modules 24 may be arranged in an array, such as in one row, two rows or more. For example, the detector modules 24 may be arranged in an array such that three rows each having nine detector modules 24 are provided.

It should be noted that number of detector housings 22 may be greater than two, for example three or more and the number of detector modules 24 may be greater or fewer. In a multi-detector camera, the position of the detector housings 22 may be, for example, substantially at 90 degrees to each other or in different configurations as known in the art.

In one embodiment, the detector modules 24 are formed from pixelated detector elements that may operate, for example, in an event counting mode and may be configured to acquire SPECT image data. The detector modules 24 may be formed from different materials, particularly semiconductor materials, such as CZT, cadmium telluride (CdTe), and silicon (Si), among others. In various embodiments, the plurality of detector modules 24 each includes detector elements having a plurality of pixels. However, it should be noted that the various embodiments are not limited to a particular type or configuration of detectors, and any suitable imaging detector may be used.

The detector modules 24 include pinhole collimation formed from pinhole collimators 50 (shown more clearly in FIG. 2) and coupled to a detecting face of the detector modules 24. The collimators 50 in some embodiments define a multi-pinhole collimator arrangement.

The detector housings 22 may be provided in different configurations, for example, in single planar imaging mode (illustrated in FIG. 1), a two detector housing 22 "L" mode configuration, multiple detector housings 22 configured along an arc (as shown in FIG. 2) an "H" mode configuration, or a three headed camera configuration, among others. Additionally, a gantry (not shown) supporting the detector housings 22 may be configured in different shapes, for example, as a "C" and the detector housings 22 may be arranged in different configurations.

The imaging system 20 also includes a detector controller 32 that operates to control the movement of the detector housings 22 about the patient 26. For example, the detector controller 32 may control movement of the detector housings 22, such as to rotate the detector housings 22 around the patient 26, and which may also include moving the detector housings closer or farther from the patient 26 and pivoting the detector housings 22. It should also be noted that in various embodiments, as described in more detail herein, the detector controller 32 is configured to control movement of a multi-layer detector 60 (as shown in FIG. 2 illustrating a single row of detector modules 24) that includes two spaced apart detector layers 62 and 64, with one of the detector layers, illustrated as detector layer 62 having an opening therethrough. For example, the detector controller 32 is configured in one embodiment to control the spacing (S) between the detector layers 62 and 64 such that the detector layers 62 and 64 may be moved closer or further apart. However, in some embodiments, the detector layers 62 and 64 are in a fixed position and orientation with respect to each other. In other embodiments, the detector layers 62 and 64 have a fixed spacing S therebetween, but are together movable.

The imaging system 20 also includes an image reconstruction module 34 configured to generate images from acquired image information 36 received from the detector housings 22. For example, the image reconstruction module 34 may operate using NM image reconstruction techniques, such as SPECT image reconstruction techniques to generate SPECT images of the patient 26, which may include an object of interest, such as the heart 38 of the patient.

Variations and modifications to the various embodiments are contemplated. For example, in a dual headed system, namely one with two detector housings 22, one detector housing 22 may include the detector modules 24 with the multiple detector layers 62 and 64 and the other detector housing 22 may include single pinhole detector arrangements or a parallel collimator detector arrangement, among others.

The image reconstruction module 34 may be implemented in connection with or on a processor 40 (e.g., workstation) that is coupled to the imaging system 20. In some embodiments, the image reconstruction module 34 may be implemented as a module or device that is coupled to or installed in the processor 40. Accordingly, the image reconstruction module 34 may be implemented in software, hardware or a combination thereof. In one embodiment, image reconstruction may be performed on a remote workstation (e.g., a viewing and processing terminal) having the processing components and not at the imaging scanner.

The image information 36 received by the processor 40 may be stored for a short term (e.g., during processing) or for a long term (e.g., for later offline retrieval) in a memory 42. The memory 42 may be any type of data storage device, which may also store different types of information. The memory 42 may be separate from or form part of the processor 40. A user input 44, which may include a user interface selection device, such as a computer mouse, trackball, touch screen, voice recognition, gesture detection and/or keyboard is also provided to receive a user input.

Thus, during operation, the output from the detector modules 24, which includes the image information 36, such as projection data from a plurality of detectors or gantry angles is transmitted to the processor 40 and the image reconstruction module 34 for reconstruction and formation of one or more images that may be displayed on a display 46. It should be noted that any suitable reconstruction method may be used.

In one embodiment, and with reference to FIG. 2, the detector modules 24 include the multiple detector layers 62 and 64 to define a dual layer SPECT detector, which is provided in a multi-gamma camera, multi-pinhole detector arrangement. In the illustrated embodiment, the detector modules 24 are arranged and supported on a support structure 52 (e.g., a scanner gantry) in a generally curved or arcuate configuration in a generally or semi-arc shape or L-shaped arrangement similar to an L-mode of operation. The detector modules 24 may be arranged to provide, for example, organ specific imaging such that each of the detector modules 24 is fixed on the support structure 52, such that the detector modules 24 conform to the shape of the patient 26. However, the detector modules 24 may be configured for other types of organ specific imaging or for general purpose imaging, and may be configured to be positionable, such that a field of view of the detector modules 24 can be adjusted during an exam or between exams.

It should be noted that the components of one of the detector modules 24 are shown in detail in FIG. 2. However, the other detector modules 24 have similar components.

The detector modules 24 include detector layers 62 and 64 that in one embodiment are each formed from one or more solid-state two-dimensional (2D) detector arrays, for example, a plurality of CZT detector arrays. Each of the detector modules 24 in this embodiment includes the pinhole collimator 50 coupled thereto such that the pinhole opening 54 of the pinhole collimator 50 generally aligns with an opening 66 through the detector layer 62. The openings 54 and 66 may be sized and shaped the same, substantially the same or differently. In one embodiment, the opening 66 is substantially larger than the opening 54. For example, the opening 66 may be sized to be about eight pixels and the opening 54 may be sized to be about one to two pixels.

Also, the openings 54 and 66 may be offset with respect to each other in at least one embodiment.

Thus, the detector layers 62 and 64 in various embodiments define a dual-detector configuration for each detector module 24. In one embodiment, the opening 66 through the detector layer 62 is located generally in the middle of the detector layer 62 with the detector layer 64 spaced apart and positioned farther away from the opening 54 of the pinhole collimator 50. Accordingly, the detector layer 64 is positioned generally behind the opening 66. In operation, the detector module 24 provides for sampling a central region (defined by the size of the opening 66) with higher resolution without loss of or with reduced loss of sensitivity (using the detector layer 64), while the outer region is sampled using the detector layer 62 at a lower resolution (to provide artifact-free or reduced artifact reconstruction). This configuration provides for a more optimal use of detector material.

It should be noted that one or more of the detector modules 24 may be positioned and oriented (e.g., angled) to focus on a region of interest, such as an organ of the patient 26 (e.g., heart, lung, brain, etc.). For example, for cardiac imaging, the detector modules 24 are positioned and oriented to focus on a location including the heart 38 of a patient 26. Thus, one or more of the detector modules 24 may be angled differently to focus on the area of interest. It also should be noted that the detector layers 62 and 64 may be formed by one or more detector elements (e.g., one or more CZT tiles) with each having a plurality of pixels (e.g., sixteen by sixteen pixels) as described in more detail herein.

The detector layers 62 and 64 may be mounted in a fixed position and orientation within the detector modules 24, for example, to the walls that form the pinhole collimator 50. The detector layers 62 and 64 may be mounted using any suitable mounting arrangement, for example, a bracket.

In other embodiments, the detector layers 62 and 64 may be mounted such that the detector layers 62 and 64 are movable with respect to each other and the opening 54. For example, the detector layers 62 and 64 may be mounted to one or more rails to allow movement within the detector module 24. In this embodiment, a base portion 63 may include a motor of other means to move the detector layer 64 towards the detector layer 62. It should be noted that any suitable actuator and drive mechanism may be used. Additionally, in other embodiments, the detector module 24 may be configured such that drive means are provided to move the detector layer 62. Accordingly, only the detector layer 62 may be configured for movement, only the detector layer 64 may be configured for movement or both of the detector layers 62 and 64 may be configured for movement. Thus, a variable focal length for the detector layers 62 and 64 is provided. Further, the motion can be used to prevent the formation of imaging artifacts related to the projection of the edge of the opening 66 in the detector layer 62 onto the surface of the detector layer 64 by ensuring that this transition is spread over a number of different lines of response for different spacings of the detector layers 62 and 64. It should be noted that such motion also provides for oversampling of the image space, which can result in improved reconstructed resolution.

In one embodiment where both of the detector layers 62 and 64 are movable, the relative distance between the two detector layers 62 and 64 is maintained constant, for example, by coupling the detector layers 62 and 64 together at a fixed distance. However, in other embodiments, the detector layers 62 and 64 may be individually and/or independently movable.

Figure 3:
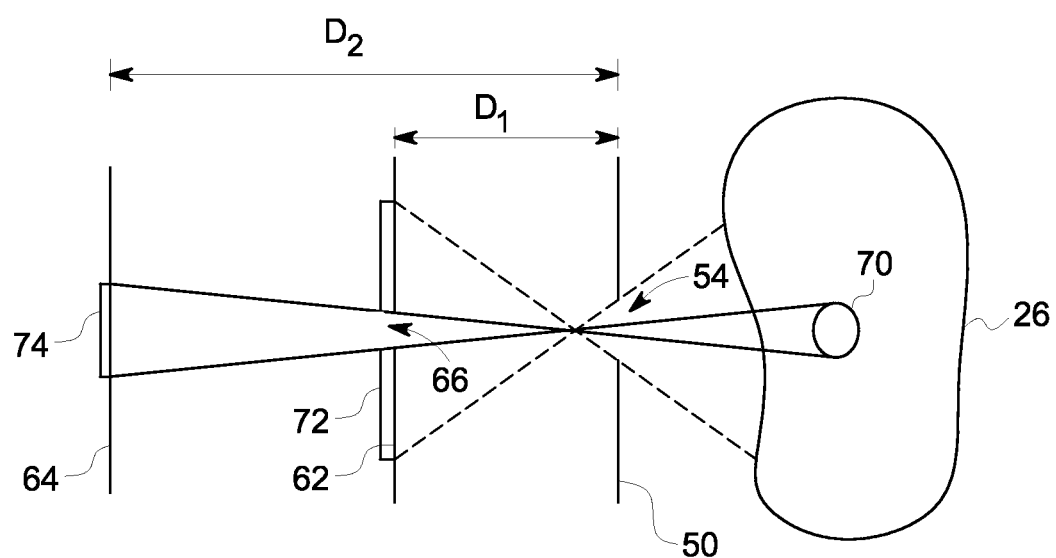
FIG. 3 is a diagram illustrating multiple detector layers in accordance with various embodiments.

FIG. 3 is simplified diagram illustrating the relationship and positioning of the detector layers 62 and 64. In particular, the detector layers 62 and 64 are spaced apart within the detector module 24 (shown in FIGS. 1 and 2) at different distances from the opening 54 of the pinhole collimator 50. As can be seen, the detector layer 62 is spaced a distance $D_1$ from the opening 54 and the detector layer 64 is spaced a distance $D_2$ from the opening 54 where $D_2$ is greater than $D_1$.

Accordingly, the different distances $D_1$ and $D_2$ define different focal lengths such that different magnifications may be provided, resulting in different resolutions. In particular, the magnification is defined by (distance to detector)/(distance to object). For example, Magnification2 (Mag2) corresponding to distance $D_2$ is $D_2/2=2*Mag1=2*D_2/D$, wherein Mag1 is the magnification corresponding to the distance $D_1$. Thus, $D_2=2*D_1$. In the illustrated embodiment, the detector layer 62 defines a lower magnification detector and the detector layer 64 defines a higher magnification detector. The lower magnification detector formed by the detector layer 62 provides sampling over a detector area 72 that is larger than the sampling area 74 of the higher magnification detector formed by the detector layer 64. Accordingly, the detector layer 62 forms a lower magnification detector over a larger area (e.g., corresponding to a less relevant region of the patient 26) and the detector layer 64 forms a higher magnification detector over a smaller area (e.g., corresponding to a more relevant region of the patient 26, illustrated as the region of interest 70).

Figure 4:
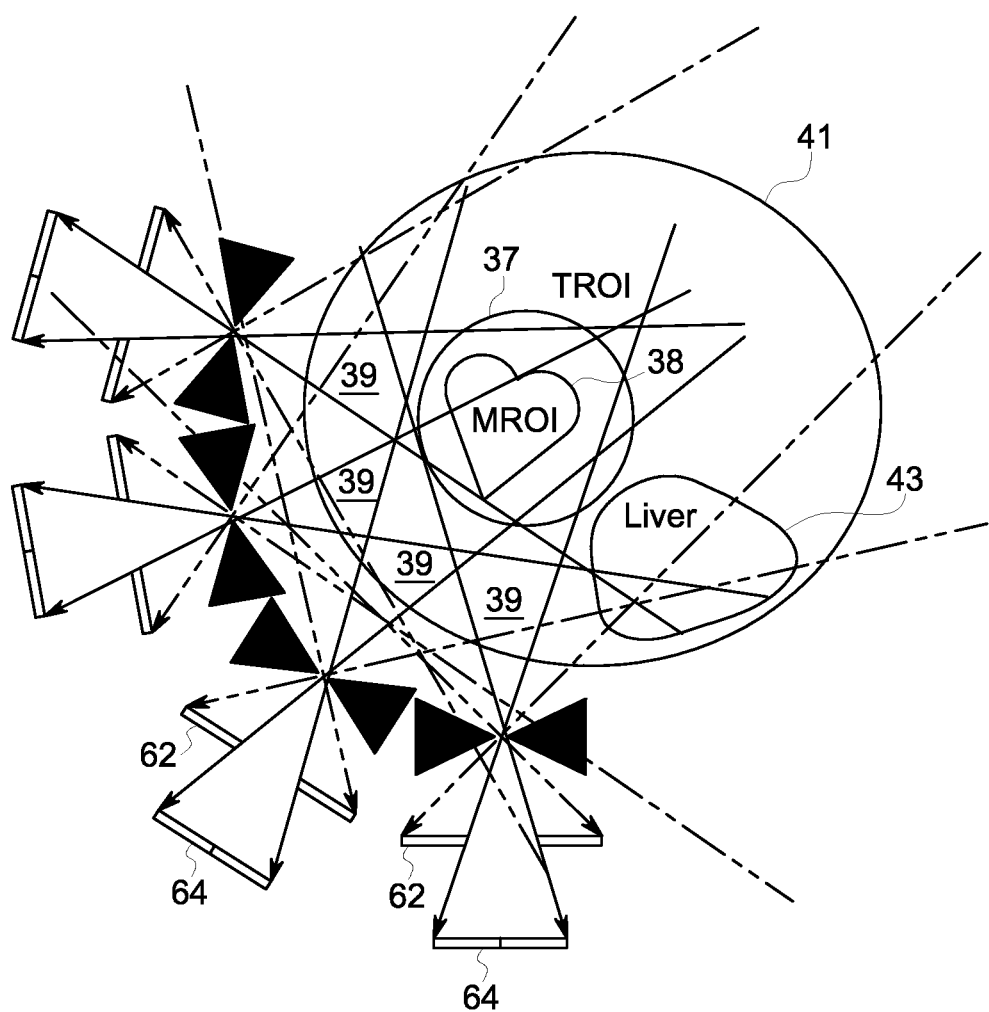
FIG. 4 is a diagram illustrating different regions of interest provided in accordance with various embodiments.

As shown in FIG. 4, the various embodiments may be used for imaging the patient 26, wherein the ROI may be smaller than the patient 26 (but usually slightly larger than the Organ Of Interest OOI, for example, the heart 38.) The ROI is then reconstructed to a 3D image. The ROI in various embodiments is within all (or at least most of the FOVs 39 of the detector modules 24. The FOVs 39 are not the same for all of the detector modules 24, and each includes more than the ROI. Thus, the overlap of the FOVs 39 defines the ROI.

In various embodiments, each FOV 39 comprises two parts, a central magnified FOV (MFOV) and a total FOV (TFOV), such that the ROI may be defined as an MROI 37 and a TROI 41, respectively. Accordingly, the MROI 37 may be reconstructed with a higher resolution (e.g., smaller voxels in the 3D image). The OOI, in this example the heart 38, should be placed within the MROI 37.

In operation, when reconstructing a patient having isotope uptake out of the reconstructed field (e.g., Out Of Field Sources (OOFSs), such as the liver 43, which is near the heart 38, but is out of at least some of the FOVs 39, thus out of the ROI), these OOFSs can causes image distortion and artifacts. Using the various embodiments, the size of the FOVs 39 and the ROI is increased to encompass both (to increase the size of the ROI). Thus, various embodiments provide a large, lower resolution TROT 41, with a central, improved resolution MROI 37.

Figure 6:
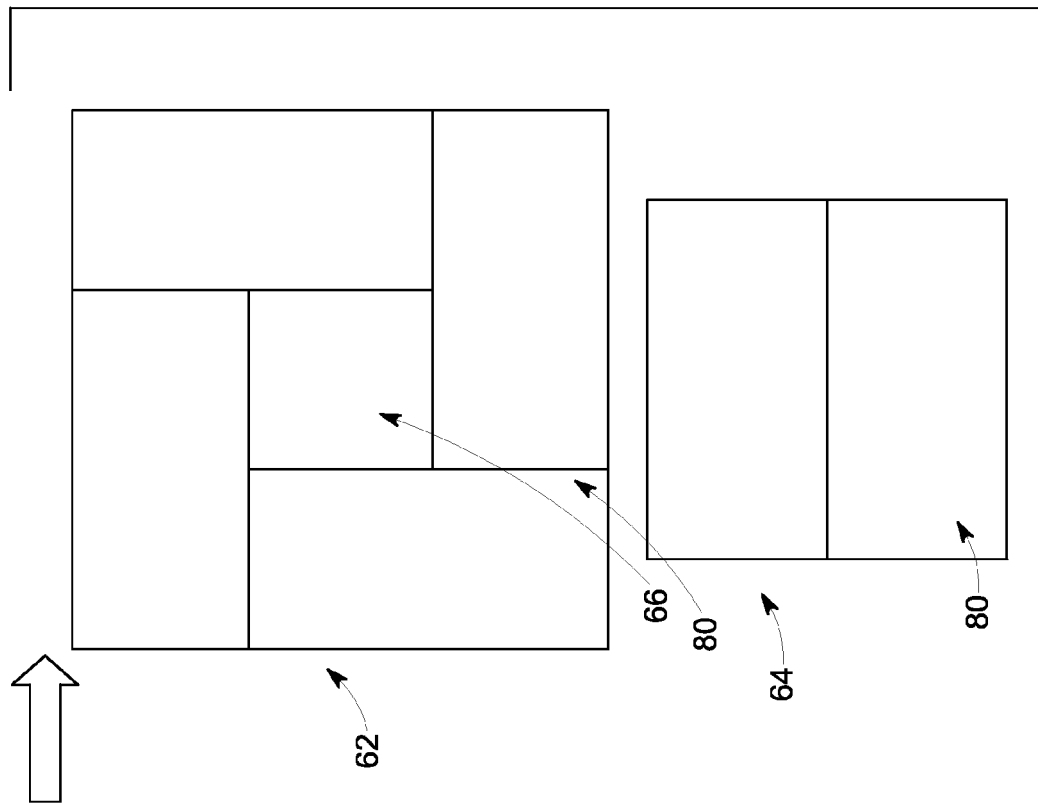
FIGS. 5 and 6 are diagrams illustrating detector tiles forming detector layers in accordance with various embodiments.
Figure 5:
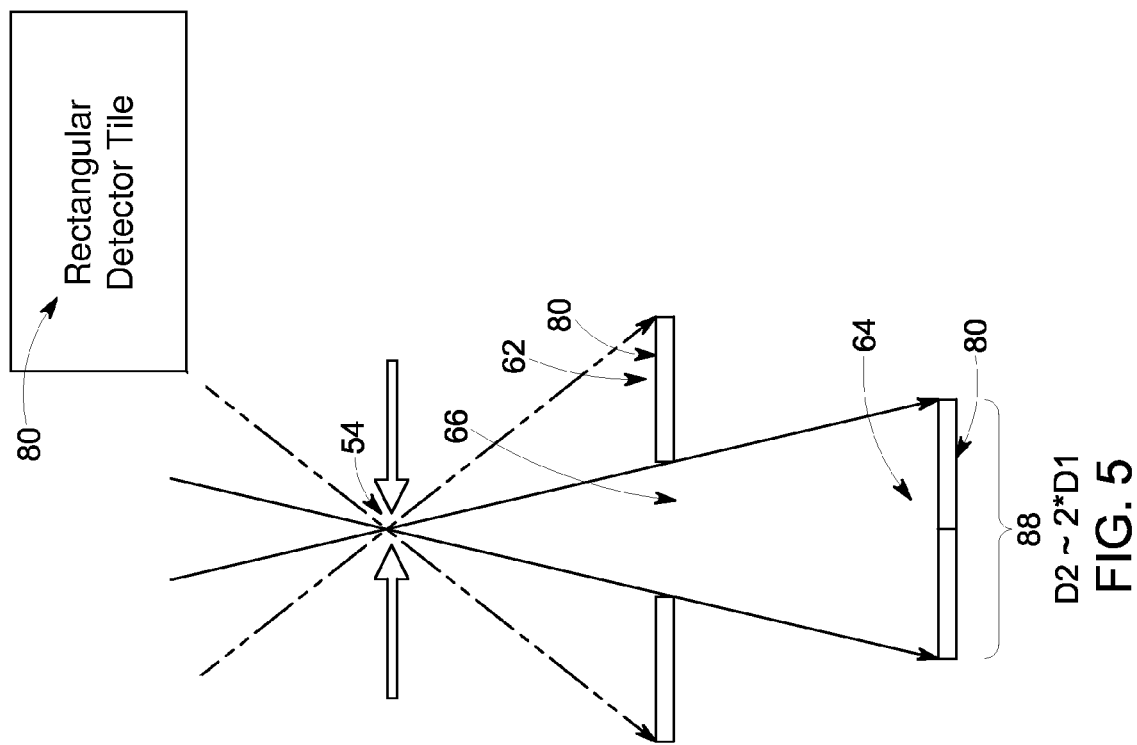

The detector layers 62 and 64 in various embodiments are formed from one or more detector elements, which are illustrated as CZT tiles 80 in FIGS. 5 and 6. In this embodiment, the detector layer 62 is formed from a plurality of rectangular shaped CZT tiles 80 arranged to define the opening 66 therethrough. In some embodiments, a size of a detection area 88 defined by the detector layer 64 is generally larger than the opening 66. For example, in various embodiments, the detector layer 64 is larger than the opening 66 by a factor of $D_1/D_2$. The detector layer 64 in one or more embodiments is the size and shape of the projection of the opening 54 through the opening 66 as illustrated in FIG. 5. In the illustrated embodiment, four CZT tiles 80 with a 2:1 aspect ratio form the opening 66 that is ⅓×⅓ of the dimensions of the detector layer 62. However, different aspect ratios may be provided as described below. Additionally, the detector layer 64 includes two CZT tiles 80, which in this embodiment are at twice the focal distance of the detector layer 62.

Figure 10:
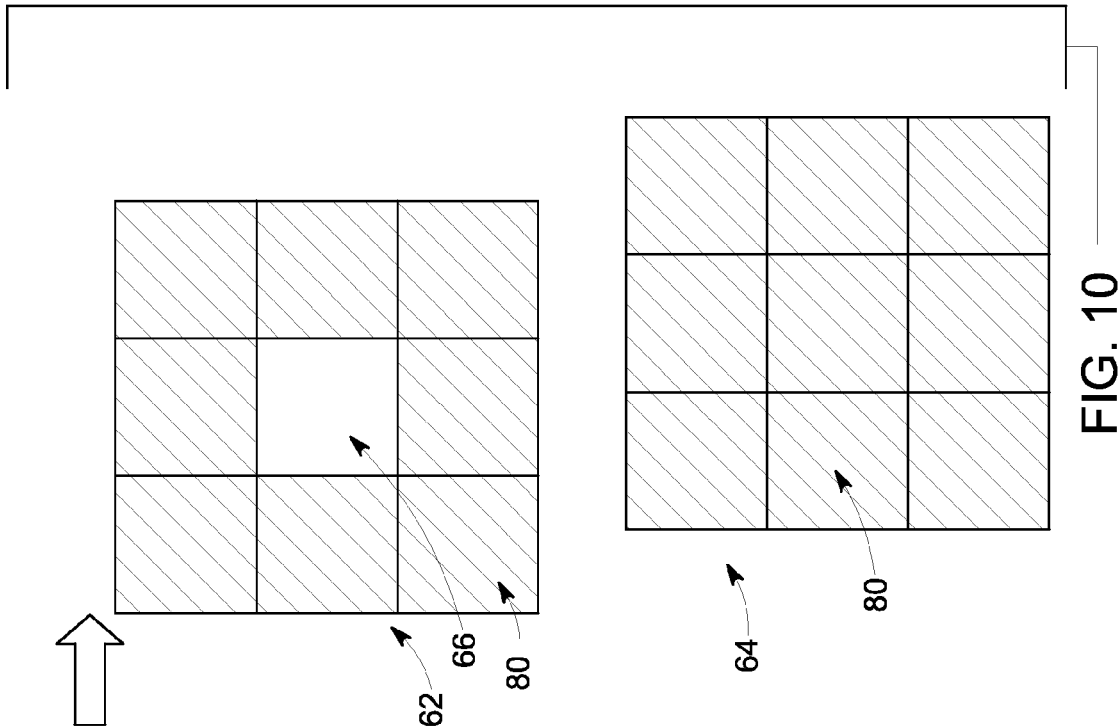
FIGS. 9 and 10 are diagrams illustrating detector tiles forming detector layers in accordance with other various embodiments.
Figure 9:
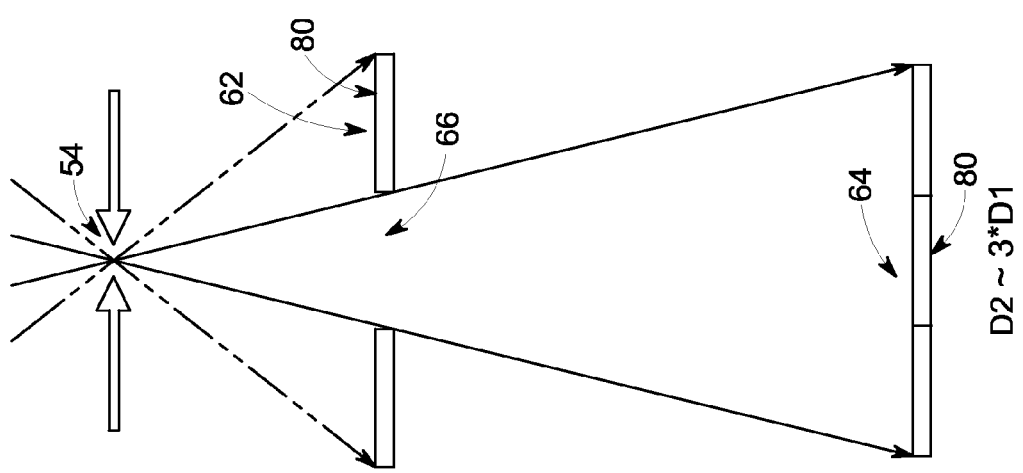

It should be noted that although all of the CZT tiles 80 are shown as having the same size and shapes, different sizes and shapes may be used for one or more of the CZT tiles 80 as desired or needed (e.g., to form a different size opening 66 or a rectangular overall shape instead of square). For example, although the CZT tiles 80 are illustrated as generally rectangular with each having 242 pixels, the CZT tiles 80 may be generally square as illustrated in FIGS. 7 and 8, wherein the detector layer 64 is formed from four CZT tiles 80. However, additional CZT tiles 80 may be used, for example, as shown in FIGS. 9 and 10, wherein the detector layer 64 is formed from nine CZT tiles 80. It should be noted that while in the embodiment of FIGS. 7 and 8, $D_2$ is approximately twice $D_1$, in the embodiment of FIGS. 9 and 10, $D_2$ is approximately three times $D_1$.

Figure 12:
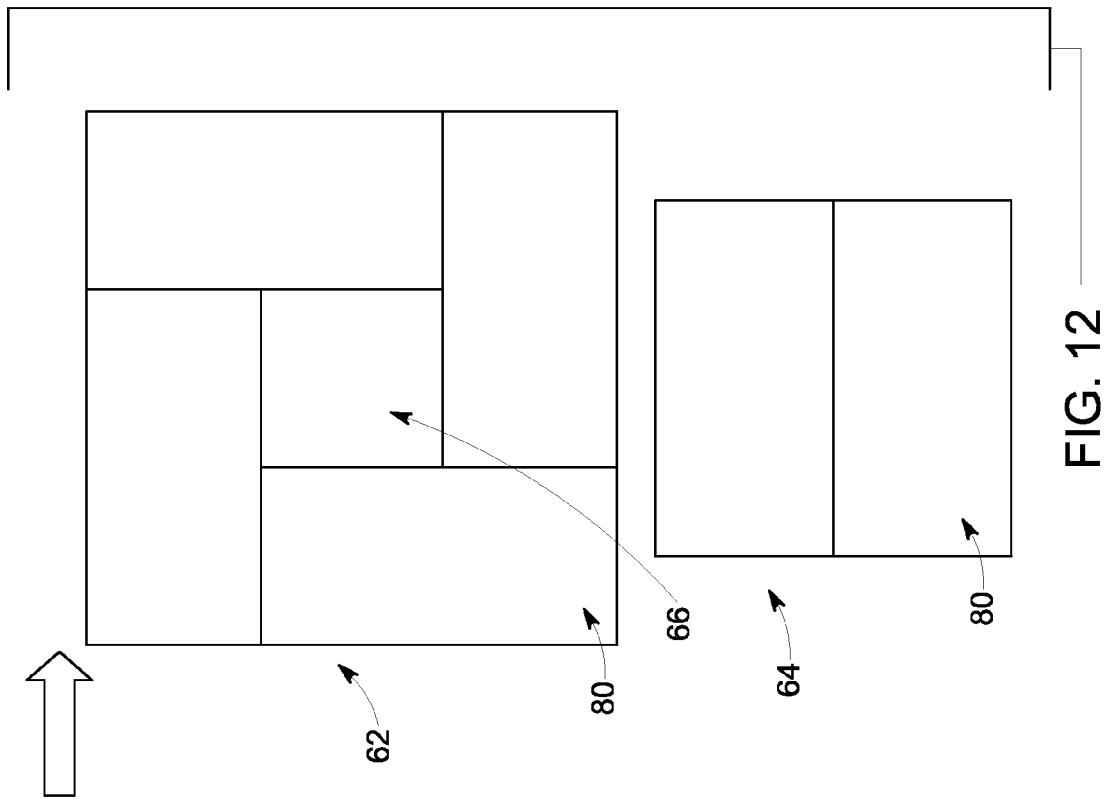
FIGS. 11 and 12 are diagrams illustrating detector tiles forming detector layers in accordance with other various embodiments.
Figure 11:
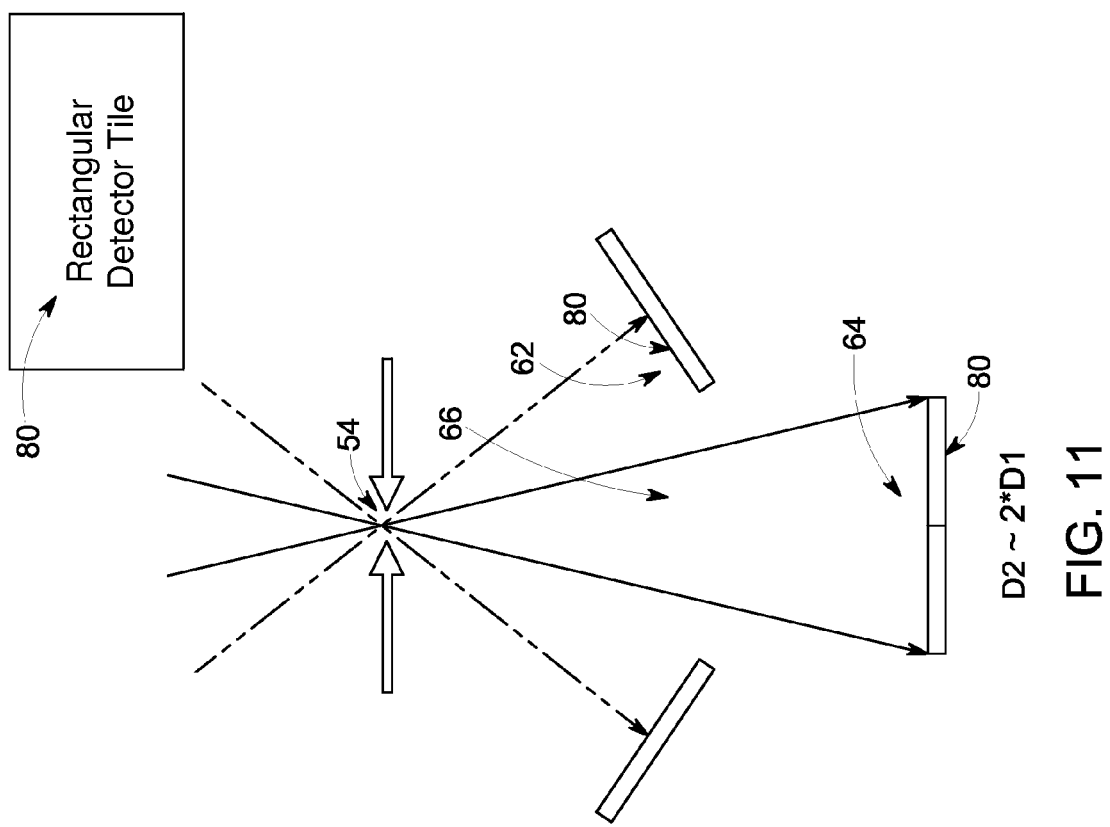
Figure 13:
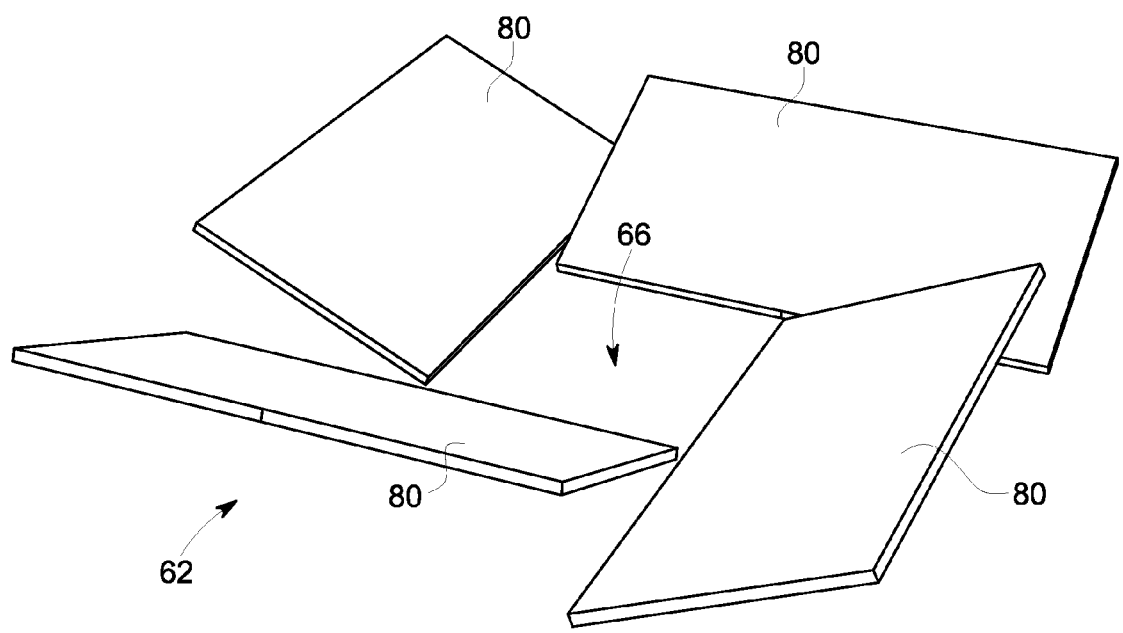
FIG. 13 is a perspective view of detector tiles of FIGS. 11 and 12.

Variations and modifications are contemplated. For example, although the detector layers 62 and 64 are shown as generally parallel, the detector layer 62 may be formed from CZT tiles 80 that are tilted as shown in FIGS. 11 and 12. Thus, as can be seen, in this embodiment, the CZT tiles 80 are angled from an outer edge of the CZT tiles 80 to an inner edge of the CZT tiles 80 defining the opening 66. As can be seen more clearly in FIG. 13, all of the CZT tiles 80 are angled downward towards the opening 66 such that in various embodiments the outer edges of the CZT tiles 80 are at one plane and the inner edges of the CZT tiles 80 are at another lower plane closer to the detector layer 64.

As still another example of a different embodiment as illustrated in FIGS. 14 and 15, the CZT tiles 80 forming the detector layer 62 may be provided generally perpendicular to the CZT tiles 80 that form the detector layer 64. In this embodiment, the CZT tiles 80 form a box-shaped or U-shaped configuration wherein the resolution on the side walls 81 is less than on the bottom defined by the detector layer 64.

Figure 19:
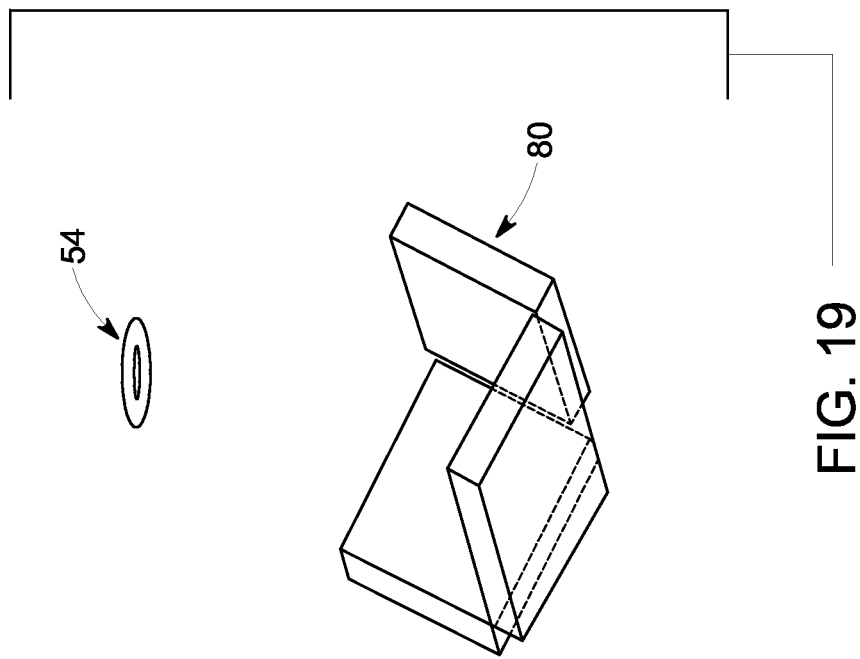
FIGS. 18 and 19 are diagrams illustrating detector tiles forming detector layers in accordance with other various embodiments.
Figure 18:
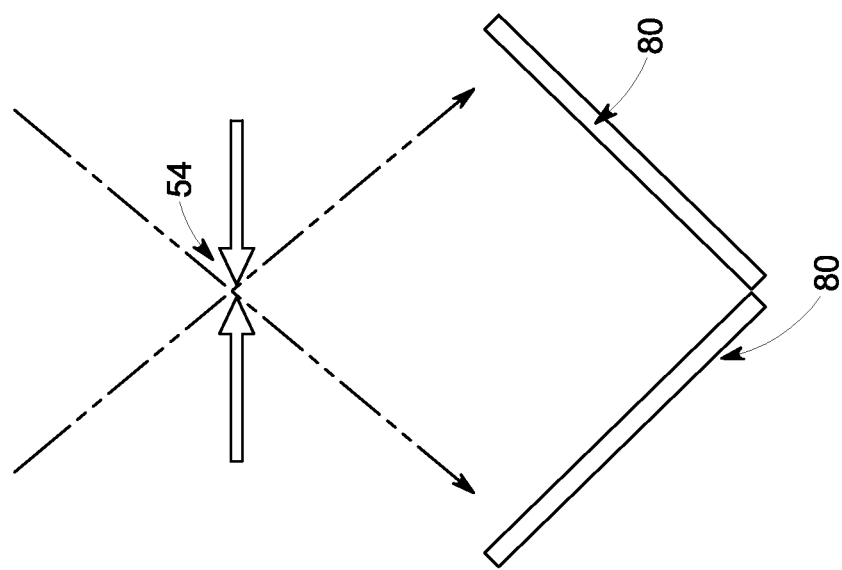
Figure 20:
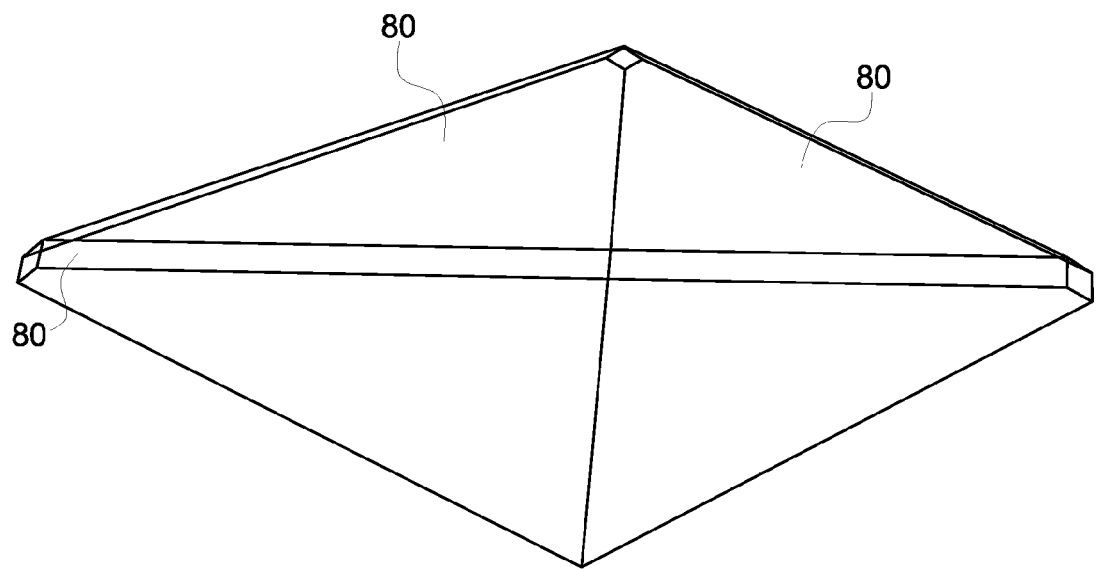
FIG. 20 is a diagram illustrating detector tiles forming a detector layer in accordance with other various embodiments.

As yet another example of a different embodiment as illustrated in FIGS. 16 and 17, only the detector layer 62 is provided. In this embodiment, the CZT tiles 80 foiin a generally V-shaped configuration with resolution increasing further down the CZT tiles 80 away from the opening 54. In one embodiment, the V-shaped configuration is formed from three square CZT tiles 80 that form a "cut-off" cube corner as shown in FIGS. 18 and 19. However, other shapes may be used. Thus, the configuration shown in FIGS. 18 and 19 define a generally corner-cube shaped configuration. The V-shaped configuration can be a one-dimensional V-shape using two detector tiles 80 or can be formed from three of more CZT tiles 80, such as square shaped (as shown in FIGS. 18 and 19) or triangular shaped detector CZT tiles 80 with a 90 degree angle facing into a vertex as shown in FIG. 20. In various embodiments using four or more detector tiles 80, the angle at the vertex or tip is less than 90 degrees.

Figure 22:
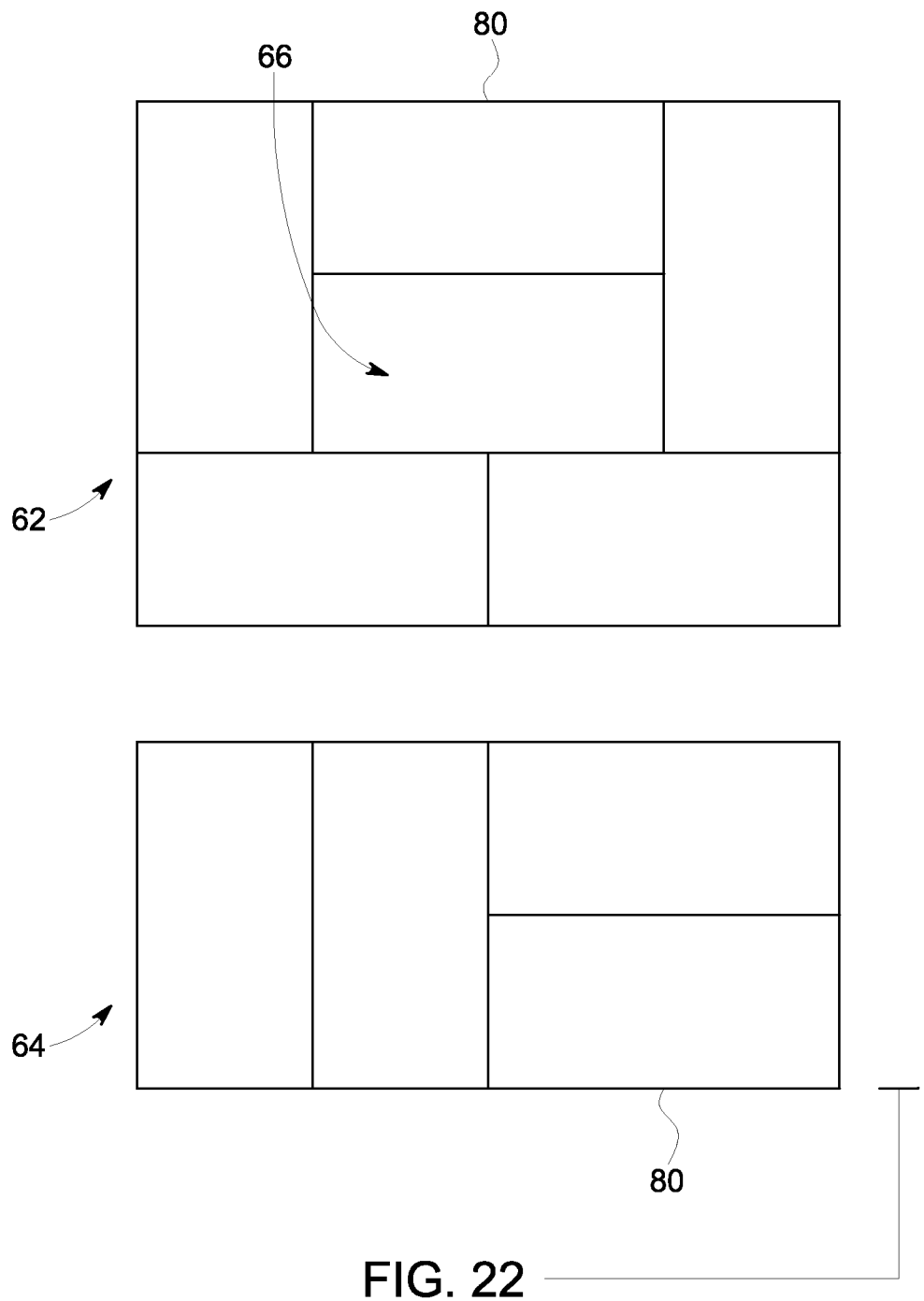
FIG. 22 is a diagram illustrating detector tiles forming detector layers in accordance with other various embodiments.

Thus, the CZT tiles 80 forming the detector layer 62 in some embodiments are generally aligned in a ring-type configuration such that each CZT tile 80 abuts an adjacent or neighboring CZT tile 80 generally perpendicularly. Thus, one end 82 of each CZT tile 80 generally abuts a side 86 of another CZT tile 80 and the other end of each CZT tile 80 forms a portion of an outer dimension or wall of the detector layer 62 with a side 86 of another adjacent CZT tile 80. However, it should be noted that one or more of the CZT tiles 80 may be shifted such that the size and/or shape of the opening 66 is changed. However, in this variation, the sides of the detector layer 62 may no longer be planar as shown in FIG. 21. In this embodiment, the size of the opening 66 is changed such that a 2:3 aspect ratio is provided. Additionally, as shown in FIG. 22, more CZT tiles 80 may be provided to increase the size of the opening 66 and/or the size of the detector layer 64 (which includes different abutting arrangements of CZT tiles 80, namely abutting along ends and/or side thereof). In this embodiment, the opening 66 has an aspect ratio of 2:1.

Accordingly, in some embodiments detection magnification may be doubled in the center of the detector module 24 (corresponding to the detection area 88). However, it should be noted that different focal distances may be used. As described herein, the detector layers 62 and 64 may be fixed at the focal distances or movable.

Thus, in various embodiments, a reduced number of CZT tiles 80 may be used to provide a same amount of detector magnification. The CZT tiles 80 may be formed from a direct conversion material (e.g., CdTe or CZT). It should be noted that as used herein, a direct conversion detector material generally refers to any detector material that directly converts (in a single conversion step) photons or other high frequency gamma ray energy to electrical signals instead of in a multi-step process such as when using a scintillator (e.g., NaI:Tl (thallium-doped sodium iodide)) and a photo-conversion device (e.g., a photo-diode). However, various embodiments may also be implemented with materials that are not direct conversion materials.

Figure 23:
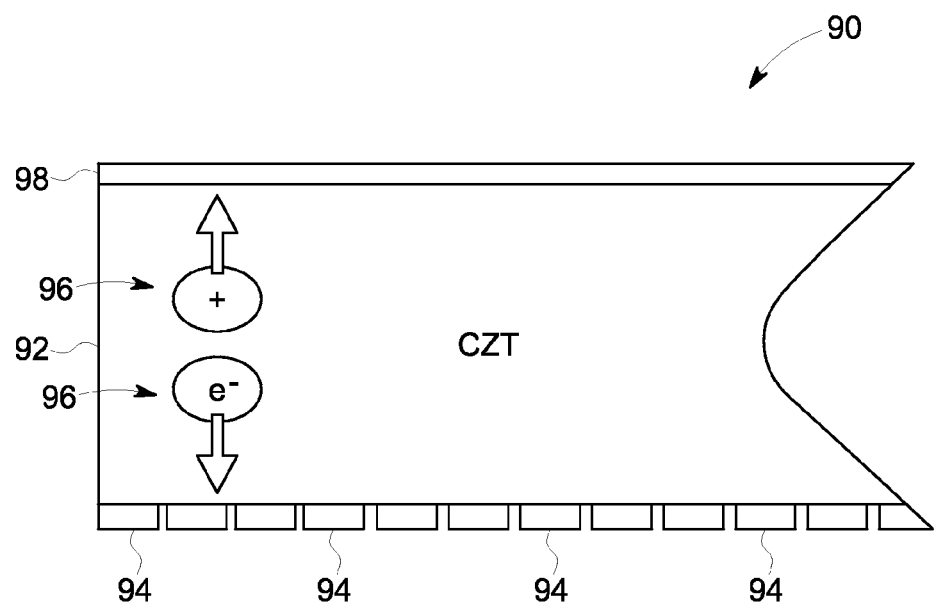
FIG. 23 is a simplified cross-sectional view of a portion of a pixelated detector element.

The CZT tile(s) 80 may be formed from pixelated detector elements 90 as shown in FIG. 23, illustrating a simplified cross-sectional elevation view of a portion of one pixelated detector element 90 formed in accordance with various embodiments. The pixelated detector element 90 includes a crystal 92 formed from a radiation responsive semiconductor material, which in various embodiments is a direct conversion material, for example, a CZT crystal. A pixelated structure having a plurality of pixels is defined, for example, by photolithography or by cutting or dicing of the contact metal on one surface or side of the crystal 92 to form a plurality of pixel electrodes, identified as anodes 94. In operation, a charge in the pixel electrodes, namely the anodes 94 is induced from a large number of electron-hole pairs 96 generated from a detected photon that is absorbed in the crystal 92.

The pixelated detector element 90 also includes a cathode 98 on an opposite surface or side of the crystal 92 from the anodes 94 and which may be formed from a single cathode electrode. It should be noted that the anodes 94 generally define the pixels of the pixelated detector element 90. It also should be noted that one or more collimators may be provided in front of a radiation detecting surface defined by the cathode 98 as described in more detail herein.

Figure 24:
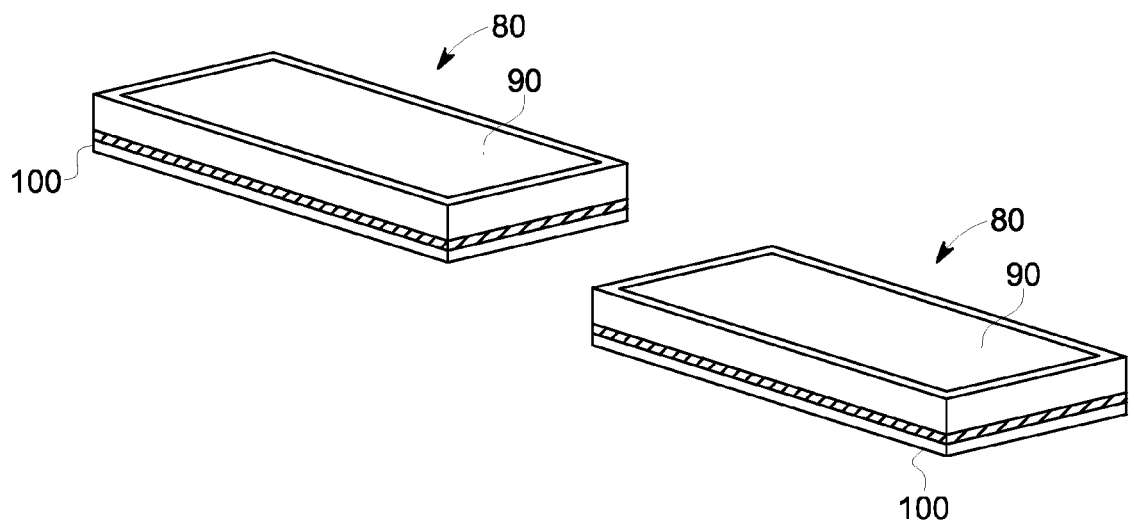
FIG. 24 is a perspective view of a detector tiles in accordance with an embodiment.

Thus, as shown in FIG. 24 a plurality of CZT tile(s) 80 that define sensor tiles may be combined to form the detector layer 62 and/or the detector layer 64 as described in more detail herein. The plurality of CZT tile(s) 80 are shown mounted on a substrate 100 that is coupled to processing and/or communication circuitry using any suitable method. Thus, in operation, the energy of a photon detected by the pixelated detector element 90 is generally determined from an estimate of the total number of electron-hole pairs produced in the crystal 92 forming the pixelated detector element 90 when the photon interacts with the material of the crystal 92. This count is generally determined from the number of electrons produced in the ionizing event, which is estimated from the charge collected on the anode of the pixelated detector element 90.

It should be noted that the plurality of CZT tile(s) 80 may be coupled together using any suitable process to form the detector layer 62 and/or the detector layer 64. It also should be noted that in some embodiments the detector layer 62 and/or the detector layer 64 may be formed from a single CZT tile 80. For example, the detector layer 62 may be formed from a single CZT tile 80 with the opening 66 cut therethrough.

Figure 25:
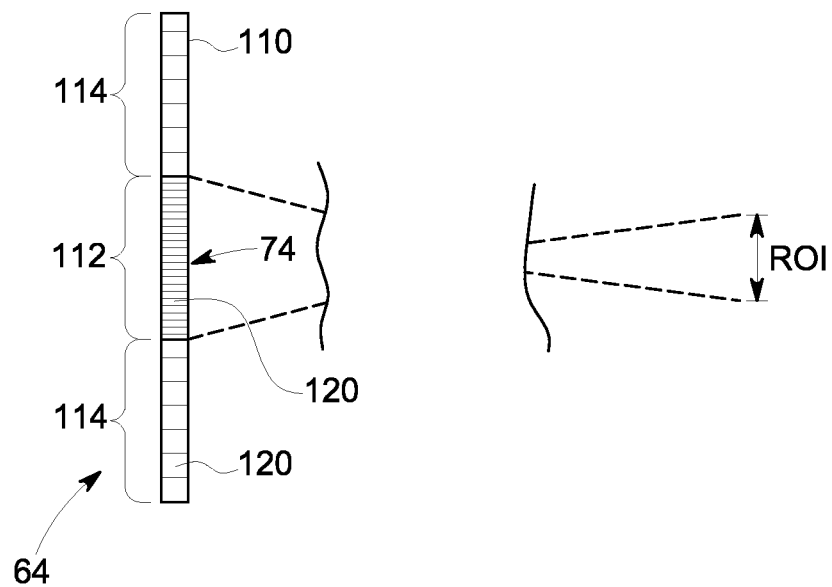
FIG. 25 is a diagram illustrating a detector layer formed in accordance with other various embodiments.

Variations and modifications are contemplated. For example, the structure of the detector layer 62 and/or the detector layer 64 may be modified. In one embodiment, as shown in FIG. 25, the detector layer 64 may be formed from a pixelated detector element 110 that has different pixelation patterns or arrangements along different portions of the pixelated detector element 110. For example, in the illustrated embodiment, a central portion 112 of the pixelated detector element 110 corresponding to the sampling area 74 may have a greater number of pixels 120 per area than the portions 114. In various embodiments, the density of the pixels 120 in the central portion 112 is greater than the portions 114, such that a finer pixelation is provided in the central portion 112 and a coarser pixelation is provided in the portions 114, thereby defining a variable pixel density. It should be noted that the length and positioning of the finer pixelation may be varied as desired or needed.

Thus, various embodiments provide detector configurations wherein the distance of the detector material to or from the collimator opening (e.g., pinhole opening) varies in a manner that is different than it would be for a planar detector. Accordingly, various embodiments provide a larger FOV and have reduced resolution in less relevant areas (e.g., less diagnostically relevant areas), and use less detector material for covering the field of view without sacrificing resolution in the MFOV.

Figure 26:
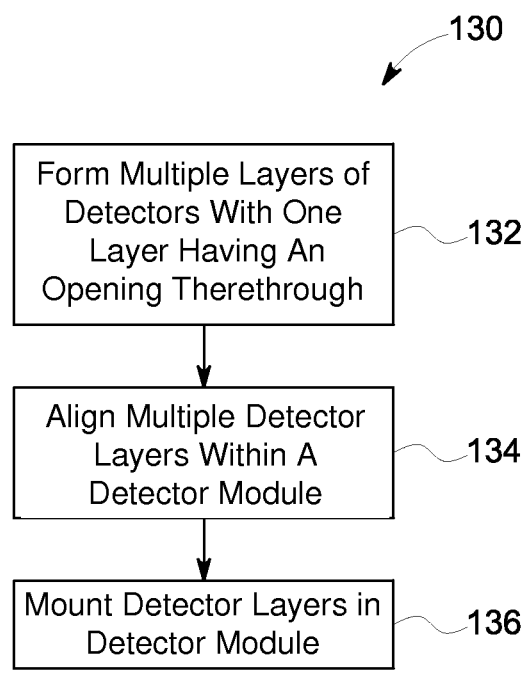
FIG. 26 is a flowchart of a method for manufacturing an imaging detector in accordance with various embodiments.

Various embodiments also provide a method 130 as shown in FIG. 26 for manufacturing a detector, such as a SPECT gamma camera. The method includes forming multiple detector layers with one layer having an opening therethrough. For example, as described herein, multiple CZT tiles may be used to form a dual layer SPECT detector wherein the CZT tiles forming one of the layers are arranged to provide an opening therethrough. The CZT tiles may be coupled together using any suitable process and may be mounted, for example, on a substrate.

The multi-layer detector, which in one embodiment is a dual layer detector structure, is aligned within a detector module at 134. For example, the detector layers may be aligned within a pinhole detector module with the detector layer having the opening closer to the pinhole opening.

The detector layers are then mounted within the detector module at 136. For example, the detector layers may be mounted in a fixed location or position within the pinhole detector module or may be mounted to be movable as described herein.

Figure 27:
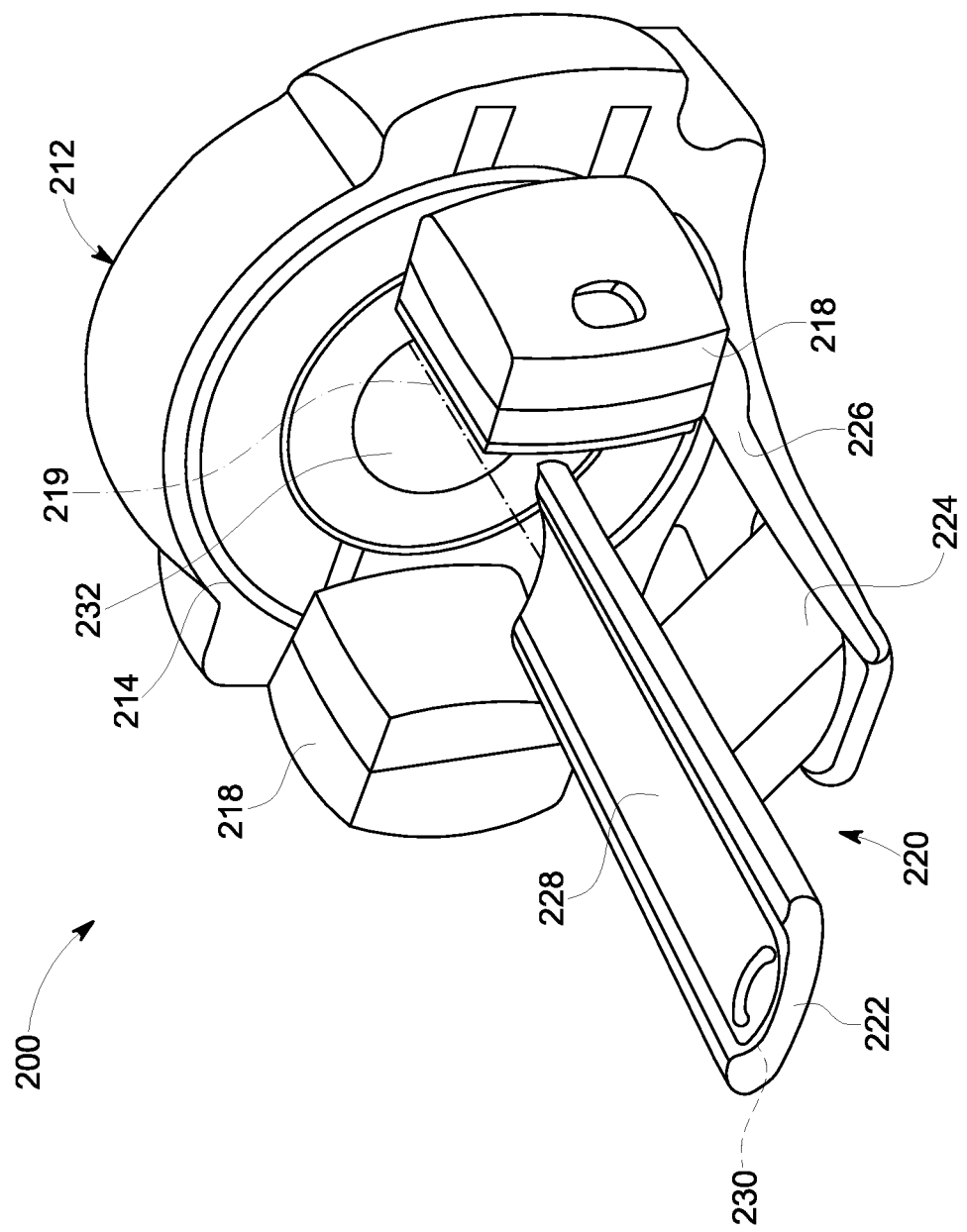
FIG. 27 is a perspective view of a Nuclear Medicine (NM) imaging system formed in accordance with various embodiments.

The detectors of various embodiments may be provided as part of different types of imaging systems, for example, NM imaging systems such as SPECT imaging systems having different detector configurations. For example, FIG. 27 is a perspective view of an exemplary embodiment of a medical imaging system 200 constructed in accordance with various embodiments, which in this embodiment is a SPECT imaging system. The system 210 includes an integrated gantry 212 that further includes a rotor 214 oriented about a gantry central bore 232. The rotor 214 is configured to support one or more NM cameras 218 (two cameras 218 are shown). The NM cameras 218 may be provided similar to the detector housings 22 as described herein.

In various embodiments, the cameras 218 are formed from pixelated detectors. However, the cameras 218 also may be formed from a continuous detector material (e.g., NaI:Tl scintillator). The rotors 214 are further configured to rotate axially about an examination axis 219.

A patient table 220 may include a bed 222 slidingly coupled to a bed support system 224, which may be coupled directly to a floor or may be coupled to the gantry 212 through a base 226 coupled to the gantry 212. The bed 222 may include a stretcher 228 slidingly coupled to an upper surface 230 of the bed 222. The patient table 220 is configured to facilitate ingress and egress of a patient 26 (shown in FIG. 1) into an examination position that is substantially aligned with examination axis 219. During an imaging scan, the patient table 220 may be controlled to move the bed 222 and/or stretcher 228 axially into and out of a bore 232. The operation and control of the imaging system 200 may be performed in any suitable manner. It should be noted that the various embodiments may be implemented in connection with imaging systems that include rotating detectors (where a gantry having a stator and a rotor coupled the detectors includes rotation of the stator) or stationary detectors.

The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as an optical disk drive, solid state disk drive (e.g., flash RAM), and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program, which may form part of a tangible non-transitory computer readable medium or media. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A nuclear medicine (NM) imaging detector comprising:
a first detector layer within a detector module;
a second detector layer within the detector module and spaced apart from the first detector layer, the second detector layer having an opening therethrough; and
a collimator mounted to the detector module, the collimator being one of a single pinhole collimator or a multi-pinhole collimator, and wherein the second detector layer is mounted within the detector module closer to an opening of the collimator than the first detector layer.

2. The NM imaging detector of claim 1, wherein the second detector layer is formed from a plurality of detector tiles arranged in a ring configuration to form the opening therethrough.

3. The NM imaging detector of claim 2, wherein the plurality of detector tiles comprise pixelated Cadmium Zinc Telluride (CZT) detector elements.

4. The NM imaging detector of claim 2, wherein the plurality of detector tiles are arranged having an aspect ratio of about 2:1.

5. The NM imaging detector of claim 1, wherein the first and second detector layers are fixedly mounted within the detector module.

6. The NM imaging detector of claim 1, wherein the first and second detector layers are movably mounted within the detector module to acquire a plurality of projections with the detector module moved to a plurality of different positions with respect to the collimator.

7. The NM imaging detector of claim 1, wherein the opening of the second detector layer is aligned with the opening of the pinhole collimator.

8. The NM imaging detector of claim 1, wherein the first and second detector layers are mounted in a parallel relationship within the detector module.

9. The NM imaging detector of claim 1, wherein the first detector layer is formed from a pixelated detector element having a variable pixel density.

10. The NM imaging detector of claim 1, wherein the first detector layer is formed from two pixelated detector tiles and the second detector layer is formed from four pixelated detector tiles.

11. The NM imaging detector of claim 1, wherein the first detector layer is at twice a focal length of the second detector layer within the detector module.

12. A nuclear medicine (NM) imaging system comprising:
a gantry;
at least one imaging detector supported on the gantry and configured to rotate about the gantry defining an axis of rotation; and
at least one detector module forming the imaging detector, the detector module including a first detector layer and a second detector layer spaced apart from the first detector layer, the second detector layer having an opening therethrough, the detector module also including a pinhole collimator mounted thereto, wherein the second detector layer is mounted within the detector module closer to the pinhole collimator than the first detector layer.

13. The NM imaging system of claim 12, wherein the second detector layer is formed from a plurality of detector tiles arranged in a ring configuration to form the opening therethrough, the detector tiles comprising one or more pixelated Cadmium Zinc Telluride (CZT) detector elements.

14. The NM imaging system of claim 12, wherein the first and second detector layers are fixedly mounted within the detector module.

15. The NM imaging system of claim 12, wherein the first and second detector layers are movably mounted within the detector module.

16. The NM imaging system of claim 12, wherein the opening of the second detector layer is aligned with the opening of the pinhole collimator, with the first and second detector layers are mounted in a parallel relationship within the detector module.

17. The NM imaging system of claim 12, wherein the first detector layer is formed form a pixelated detector element having a variable pixel density.

18. The NM imaging system of claim 12, wherein the first detector layer is at twice a focal length of the second detector layer within the detector module.

19. A nuclear medicine (NM) imaging system comprising:
at plurality of imaging detectors; and
at least one detector module forming each of the imaging detectors, the detector module including a first detector layer and a second detector layer spaced apart from the first detector layer, the second detector layer having an opening therethrough, the detector module also including a pinhole collimator mounted thereto, wherein the second detector layer is mounted within the detector module closer to the collimator than the first detector layer.

20. The NM imaging system of claim 19, further comprising a gantry and wherein the plurality of imaging detectors are configured to rotate about the gantry defining an axis of rotation.

21. The NM imaging system of claim 19, wherein the plurality of imaging detectors are stationary with respect to an imaged object during imaging.

22. A method of manufacturing a detector, the method comprising:
forming multiple detector layers with at least one layer having an opening therethrough;
aligning the multiple detector layers spaced apart within a detector module; and
mounting the detector layers within the detector module with a pinhole collimator mounted thereto, the detector layer with the opening mounted closer to an opening of the pinhole collimator.

23. The method of claim 22, wherein forming the multiple layers comprises forming the layer with the opening from a plurality of detector tiles arranged in a ring configuration to form the opening.

* * * * *